US006534625B2

(12) United States Patent
Matsumoto et al.

(10) Patent No.: US 6,534,625 B2
(45) Date of Patent: Mar. 18, 2003

(54) PROCESS FOR PRODUCING HYDROXYALKYL (METH)ACRYLATE

(75) Inventors: Hajime Matsumoto, Himeji (JP); Tokumasa Ishida, Himeji (JP); Yukihiro Yoneda, Himeji (JP)

(73) Assignee: Nippon Shokubai Co., Ltd, Osaka (JP)

( * ) Notice: Subject to any disclaimer, the term of this patent is extended or adjusted under 35 U.S.C. 154(b) by 0 days.

(21) Appl. No.: 09/965,699

(22) Filed: Sep. 26, 2001

(65) Prior Publication Data

US 2002/0040125 A1 Apr. 4, 2002

(30) Foreign Application Priority Data

Sep. 29, 2000  (JP) ........................................ 2000-300771

(51) Int. Cl.[7] .................................................. C08F 6/00
(52) U.S. Cl. ..................................................... 528/499
(58) Field of Search .......................................... 528/499

(56) References Cited

U.S. PATENT DOCUMENTS

| 3,340,295 A | 9/1967 | Wheeler et al. |
| 3,804,884 A | 4/1974 | Jeffrey et al. |
| 4,028,070 A | 6/1977 | Uchii et al. |

FOREIGN PATENT DOCUMENTS

| JP | 41-13019 | 7/1966 |
| JP | 43-18890 | 8/1968 |
| JP | 10-330320 A | 12/1998 |
| JP | 11-240853 A | 9/1999 |

*Primary Examiner*—Terressa M. Boykin
(74) *Attorney, Agent, or Firm*—Haugen Law Firm PLLP

(57) ABSTRACT

The present invention provides a process for producing a hydroxyalkyl (meth)acrylate which comprises the step of carrying out a reaction between (meth)acrylic acid and an alkylene oxide, wherein the process provides enablement for economically and efficiently recovering and recycling the unreacted residue of the alkylene oxide. The process for producing a hydroxyalkyl (meth)acrylate comprises the steps of, carrying out a reaction between (meth)acrylic acid and an alkylene oxide; stripping the unreacted residue of the alkylene oxide from the resultant reaction liquid; and causing a solvent to absorb the stripped alkylene oxide; wherein: water is used as the absorbing solvent; and an absorbing liquid resultant from the absorption of the unreacted residue of the alkylene oxide is used for production of an alkylene glycol.

7 Claims, No Drawings

PROCESS FOR PRODUCING HYDROXYALKYL (METH)ACRYLATE

BACKGROUND OF THE INVENTION

1. Technical Field

The present invention relates to a process for producing a hydroxyalkyl (meth)acrylate, which comprises the step of carrying out a reaction between (meth)acrylic acid and an alkylene oxide.

2. Background Art

As to processes for producing a hydroxyalkyl (meth)acrylate which comprise the step of carrying out a reaction between (meth)acrylic acid and an alkylene oxide, it is known that the alkylene oxide is supplied to a reactor in a molar quantity excessive to (meth)acrylic acid so that the formation of by-products, such as alkylene glycol di(meth)acrylate (which might hereinafter be referred to as diester) and dialkylene glycol mono(meth)acrylate, can be inhibited, and so that the conversion of (meth)acrylic acid can be enhanced as much as possible (e.g. JP-B-013019/1966, JP-B-018890/1968). In this case, the unreacted residue of the alkylene oxide is present in the resultant reaction liquid at the end of the reaction, Therefore, after being separated from the reaction liquid, this residue needs to be disposed of, or recovered and recycled.

However, in the case where the alkylene oxide, as separated from the reaction liquid by such as stripping, is condensed by cooling for the above recovery and recycling, the cooling needs so great a deal of energy as to be economically disadvantageous.

In addition, JP-A-330320/1998 discloses that the unreacted residue of the alkylene oxide can be effectively utilized by causing it to be absorbed into raw (meth)acrylic acid and then recycling the resultant alkylene-oxide-containing (meth)acrylic acid to the reaction. However, the amount of (meth)acrylic acid as the absorbing solvent is limited by the molar ratio of the reaction, therefore this prior art cannot be said to be on a sufficiently satisfactory level in respect to the recovery efficiency.

SUMMARY OF THE INVENTION

A. Object of the Invention

An object of the present invention is to provide a process for producing a hydroxyalkyl (meth)acrylate which comprises the step of carrying out a reaction between (meth)acrylic acid and an alkylene oxide, wherein the process provides enablement for economically and efficiently recovering and recycling the unreacted residue of the alkylene oxide.

B. Disclosure of the Invention

The present inventors diligently studied to solve the above problems. As a result, the inventors directed their attention to stripping the unreacted residue of the alkylene oxide from the reaction liquid to separate therefrom the unreacted residue of the alkylene oxide, and then using water as an absorbing solvent to cause it to absorb the separated unreacted residue of the alkylene oxide. Water has advantages in that: it has a lower solidifying point than (meth)acrylic acid, therefore its absorption temperature can be set to be so low as to enhance the absorption efficiency of the unreacted residue of the alkylene oxide. In addition, water can further exhibit the economical advantage of being inexpensive. And the inventors have completed the present invention by further leading to an idea that the absorbing liquid resultant from the above absorption of the unreacted residue of the alkylene oxide is an aqueous alkylene oxide solution and therefore can be recycled as a raw material for production of an alkylene glycol.

That is to say, a process for producing a hydroxyalkyl (meth)acrylate, according to the present invention, comprises the steps of: carrying out a reaction between (meth)acrylic acid and an alkylene oxide; stripping the unreacted residue of the alkylene oxide from the resultant reaction liquid, and causing a solvent to absorb the stripped alkylene oxide; wherein:

water is used as the absorbing solvent; and an absorbing liquid resultant from the absorption of the unreacted residue of the alkylene oxide is used for production of an alkylene glycol.

These and other objects and the advantages of the present invention will be more fully apparent from the following detailed disclosure.

DETAILED DESCRIPTION OF THE INVENTION

The present invention is explained in detail below.

First, the process for producing a hydroxyalkyl (meth)acrylate to which the characteristic production process according to the present invention is favorably applicable is roughly explained as follows.

First, an addition reaction between (meth)acrylic acid and the alkylene oxide is carried out in the presence of a catalyst. The conversion in this addition reaction is often less than 100%, therefore generally such as the unreacted residue of the (meth)acrylic acid or alkylene oxide is present in the resultant reaction liquid at the end of the reaction. Thus, the above reaction liquid is led to the step to remove such as these unreacted residues of raw materials from the reaction liquid, and then purified by such as distillation as the subsequent final step, with the result that the aimed hydroxyalkyl (meth)acrylate is obtained.

When the present invention is carried out, the amount of raw materials as charged for the above reaction between (meth)acrylic acid and the alkylene oxide is such that the alkylene oxide is favorably in the range of 1.0 to 5.0 mols, more favorably in the range of 1.0 to 3.0 mols, still more favorably in the range of 1.0 to 2.0 mols, per 1 mol of (meth)acrylic acid. In the case where the amount of the alkylene oxide as charged is smaller than 1.0 mol, there are disadvantages in that the conversion of (meth)acrylic acid is lowered to increase the by-products. In addition as the amount of the alkylene oxide as charged is increased from 1 mol, the formation of the by-products can be inhibited more and more. However, in the case where the amount of the alkylene oxide as charged is larger than 5 mols, there are economical disadvantages.

When carrying out the present invention, the catalyst used for the above reaction between (meth)acrylic acid and the alkylene oxide is not especially limited, but, for example, conventional homogeneous or heterogeneous catalysts for addition reactions can be used.

In addition, conventional polymerization inhibitors are usable as stabilizers for the reaction liquid. Examples thereof include: phenol compounds such as hydroquinone, methylhydroquinone, tert-butylhydroquinone, 2,6-di-tert-butylhydroquinone, 2,5-di-tert-butylhydroquinone, 2,4-dimethyl-6-tert-butylphenol, hydroquinone monomethyl ether, cresol, and tert-butylcatechol; paraphenylenediamines such as N-isopropyl-N'-phenyl-para-phenylenediamine, N-(1,3-dimethylbutyl)-N'-phenyl-para-phenylenediamine, N-(1-methylheptyl)-N'-phenyl-para-phenylenediamine, N,N'-diphenyl-para-phenylenediamine, and N,N'-di-2-naphthyl-para-phenylenediamine; amine compounds such as thiodiphenylamine and phenothiazine; copper dialkyldithiocarbamates such as copper dibutyldithiocarbamate, copper dipropyldithiocarbamate, copper diethyldithiocarbamate, and copper dimethyldithiocarbamate; copper diaryldithiocarbamates such as copper diphenyldithiocarbamate; nitroso compounds such as nitrosophenol, N-nitrosodiphenylamine, isoamyl nitrite, N-nitroso-cyclohexylhydroxylamine, N-nitroso-N-phenyl-N-hydroxylamine, and their salts; N-oxyl compounds such as 2,2,4,4-tetramethylazetidine-1-oxyl, 2,2-dimethyl-4,4-dipropylazetidine-1-oxyl, 2,2,5,5-tetramethylpyrrolidine-1-oxyl, 2,2,5,5-tetramethyl-3-oxopyrrolidine-1-oxyl, 2,2,6,6-tetramethylpiperidine-1-oxyl, 4-hydroxy-2,2,6,6-tetramethylpiperidine-1-oxyl, 6-aza-7,7-dimethyl-spiro(4,5)decane-6-oxyl, 2,2,6,6-tetramethyl-4-acetoxypiperidine-1-oxyl, 2,2,6,6-tetramethyl-4-benzoyloxypiperidine-1-oxyl, and 4,4',4"-tris(2,2,6,6-tetramethylpiperidine-1-oxyl) phosphite; tetraalkylthiuram disulfides such as tetrabutylthiuram disulfide, tetrapropylthiuram disulfide, tetraethylthiuram disulfide, and tetramethylthiuram disulfide; and Methylene Blue. These polymerization inhibitors may be used either alone respectively or in combinations with each other. The amount of the polymerization inhibitor as added is in the range of favorably 0.0001 to 1 weight %, more favorably 0.001 to 0.5 weight %, of (meth)acrylic acid.

In addition, if molecular oxygen is further used jointly with the polymerization inhibitor as the need arises, the polymerization inhibition effect is more enhanced.

The process for producing a hydroxyalkyl (meth)acrylate, according to the present invention, is characterized by the step of removing the unreacted residue of the alkylene oxide from the reaction liquid after the reaction between (meth)acrylic acid and the alkylene oxide in the above series of production processes, particularly, characterized by the absorption step of causing a solvent to absorb the unreacted residue of the alkylene oxide after the step of stripping the unreacted residue of the alkylene oxide and by the mode of the use of the absorbing liquid resultant from the above absorption. The characteristic production process according to the present invention is explained below.

The reaction liquid, resultant from the addition reaction between (meth)acrylic acid and the alkylene oxide, usually contains the unreacted residue of the alkylene oxide together with the hydroxyalkyl (meth)acrylate which is the aimed product This reacted liquid is supplied into a stripping apparatus favorably in a state where the temperature of the reacted liquid is kept after the reaction. Theoretically, the higher the temperature of the reacted liquid is when the reacted liquid is supplied into the stripping apparatus, the greater convenience there is for enhancing the stripping efficiency. However, re-heating the liquid containing the alkylene oxide involves a danger of explosion, therefore it is a favorable mode in which, as is mentioned above, the reacted liquid is supplied into the stripping apparatus in a state where the temperature of the reacted liquid is kept after the reaction. In addition, the temperature of the reacted liquid is limited, for example, also for the purpose of enhancing the reaction yield and inhibiting the formation of by-products, and is favorably in the range of 40 to 130° C., more favorably 50 to 90° C. The above stripping apparatus is not especially limited, but examples of those which are favorable for the enhancement of the stripping efficiency include packed columns and plate columns such as bubble cap columns and perforated-plate columns.

By vaporization under reduced pressure or by use of an inert gas, the unreacted residue of the alkylene oxide is stripped from the alkylene-oxide-containing reacted liquid as has been supplied into the stripping apparatus, and then the vaporized gas of the alkylene oxide or the alkylene-oxide-containing inert gas, resultant from this stripping, is introduced into an absorption apparatus containing an absorbing solvent. Especially, the use of the inert gas is favorable in that the danger of explosion, which is caused by the rise of the temperature due to the adiabatic compression of the alkylene oxide when feeding the unreacted-alkylene-oxide-containing gas with such as a compressor, can be avoided, with the result that a safe production process can be provided.

The alkylene oxide, as stripped from the stripping apparatus, is supplied to a subsequent absorption apparatus and then absorbed into a solvent in the absorption apparatus. The absorption apparatus is not especially limited, but examples of those which are favorable for the enhancement of the absorption efficiency include packed columns and plate columns such as bubble cap columns and perforated-plate columns.

In the alkylene oxide stripping step, the lower the operational pressure is, the better the stripping efficiency is, On the other hand, in the alkylene oxide absorption step, the higher the operational pressure is, the better the absorption efficiency is. However, the involvement of the compression when feeding the gas from the stripping apparatus to the absorption apparatus is unfavorable in that there is a danger of explosion which is caused by the rise of the temperature due to the adiabatic compression. Accordingly, it is necessary to render the operational pressure in the absorption step lower than that in the stripping step. However, if the operational pressure in the absorption step is set in the range of 1,000 to 2,000 hPa, sufficient efficiency is obtained both for the stripping and the absorption.

In the production process according to the present invention, water is used as the absorbing solvent for the unreacted residue of the alkylene oxide. The lower the absorption temperature is in the step of causing the unreacted residue of the alkylene oxide to be absorbed, the better the absorption efficiency is. However, for example, (meth)acrylic acid has so high a solidifying point of about 15° C. that the absorption temperature substantially cannot be set so as not to be higher than 20° C. However, water has so low a solidifying point of about 0° C. that the absorption temperature can be lowered to not higher than 20° C. In addition, water is so inexpensive as to be excellent also in economical advantage.

The content of components other than the alkylene oxide in the absorbing liquid resultant from the absorption of the unreacted residue of the alkylene oxide in the present invention is not especially limited. However, the lower this content is, the greater convenience there is for recycling the above absorbing liquid to the production of the alkylene glycol.

In the present invention, when the unreacted residue of the alkylene oxide is recovered by the stripping and absorption, the (meth)acrylic acid or the hydroxyalkyl (meth)acrylate mingles into the absorbing liquid as well as the absorption apparatus due to the vapor pressure or an entrainment caused by the stripping, but the (meth)acrylic acid concentration in the absorbing liquid resultant from the absorption of the unreacted residue of the alkylene oxide is favorably not more than 0.2 weight %, more favorably not more than 0.1 weight %, still more favorably not more than 0.05 weight %. In the case where the (meth)acrylic acid concentration in the absorbing liquid resultant from the absorption of the unreacted residue of the alkylene oxide is more than 0.2 weight %, (meth)acrylic acid deteriorates the product quality of the alkylene glycol when the above absorbing liquid is used for the production of the alkylene glycol. In addition, (meth) acrylic acid has an unsaturated bond in its molecule and therefore polymerizes so much easily as to tend to cause troubles such as clogging up of apparatuses in alkylene glycol facilities.

In the present invention, the hydroxyalkyl (meth)acrylate concentration in the absorbing liquid resultant from the absorption of the unreacted residue of the alkylene oxide is favorably not more than 0.5 weight %, more favorably not more than 0.3 weight % still more favorably not more than 0.1 weight %. Similarly to the above case of (meth)acrylic acid, in the case where the hydroxyalkyl (meth)acrylate concentration in the absorbing liquid resultant from the absorption of the unreacted residue of the alkylene oxide is more than 0.5 weight %, the hydroxyalkyl (meth)acrylate deteriorates the product quality of the alkylene glycol when the above absorbing liquid is used for the production of the alkylene glycol. In addition, the hydroxyalkyl (meth) acrylate has an unsaturated bond in its molecule and therefore polymerizes so much easily as to tend to cause troubles such as clogging up of apparatuses in alkylene glycol facilities.

In addition, the kind of the component other than the unreacted residue of the alkylene oxide in water which is used as the absorbing solvent in the present invention is not especially limited, but any of components such as (meth) acrylic acid, hydroxyalkyl (meth)acrylate, benzene, toluene and xylene is available.

The temperature of the above absorbing liquid in the present invention is not especially limited, but is favorably in the range of 10 to 70° C., more favorably 15 to 50° C.

In the production process according to the present invention, the aforementioned absorbing liquid resultant from the absorption of the unreacted residue of the alkylene oxide is used for production of an alkylene glycol.

Generally, an aqueous alkylene oxide solution is used as a raw material for the production of the alkylene glycol. The absorbing liquid resultant from the absorption of the unreacted residue of the alkylene oxide in the execution of the production process according to the present invention is an aqueous alkylene oxide solution and is therefore usable for the production of the alkylene glycol, so that the aforementioned unreacted residue of the alkylene oxide can be recovered and recycled effectively without being disposed of.

In the production process according to the present invention, favorably, the aforementioned absorbing liquid resultant from the absorption of the reacted residue of the alkylene oxide is mixed with an aqueous alkylene oxide solution resultant from production of an alkylene oxide and then used for the production of the alkylene glycol. Generally, the aqueous alkylene oxide solution resultant from the production of the alkylene oxide is used as an aqueous alkylene oxide solution that is used for the production of the alkylene glycol. And, in conventional production plants, the production scale of the alkylene oxide is often at least 10 times as large as that of the hydroxyalkyl (meth) acrylate Accordingly, if the above mode, in which the aforementioned absorbing liquid resultant from the absorption of the unreacted residue of the alkylene oxide is mixed with an aqueous alkylene oxide solution resultant from production of an alkylene oxide and then used for the production of the alkylene glycol, is taken, then the afore- mentioned absorbing liquid resultant from the absorption of the unreacted residue of the alkylene oxide is diluted to at least 10 times and it is therefore unnecessary to precisely (strictly) control the alkylene oxide concentration in the aforementioned absorbing liquid.

In addition, if, as is mentioned above, the aforementioned absorbing liquid resultant from the absorption of the unreacted residue of the alkylene oxide is diluted to at least 10 times, then there are advantages in that the concentrations of components other than the alkylene oxide, such as (meth) acrylic acid and hydroxyalkyl (meth)acrylate, in the above absorbing liquid is also diluted.

In the present invention, a part of the absorbing liquid resultant from the absorption of the unreacted residue of the alkylene oxide may be subjected to addition of (meth)acrylic acid or alkylene oxide fitly if necessary, and then recycled as a raw material for producing the hydroxyalkyl (meth) acrylate. Or the alkylene oxide may be separated from water (which is a solvent) and then used as a raw material for processes of producing other alkylene oxide derivatives.

As to the operational pressures in the stripping step and the absorption step, the lower the operational pressure in the stripping step is, the higher the stripping efficiency is. On the other hand, the higher the operational pressure in the absorption step is, the higher the absorption efficiency is. Therefore, as the operational pressure in the absorption step is got considerably higher than that in the stripping step, theoretically both the stripping efficiency and the absorption efficiency become better However, in the case where the operational pressure in the absorption step is got considerably higher than that in the stripping step, the stripped gas containing the alkylene oxide becomes adiabatically compressed with such as a compressor, so there occurs a danger of explosion due to the rise of the temperature. Thus, in the case where arrangements are made to maintain both the stripping efficiency and the absorption efficiency on practical use levels, the difference in operational pressure between the step of: stripping the unreacted residue of the alkylene oxide from the resultant reaction liquid and the step of causing the stripped unreacted residue of the alkylene oxide to be absorbed is favorably not more than 1,000 hPa, so that the alkylene oxide can safely and efficiently be stripped and absorbed. In addition, in the case where the inert gas is recycled, it is necessary to raise the pressure in order to return the gas (as discharged from the absorption apparatus) to the stripping apparatus. Also in this case, from the viewpoint of the safety it is favorable that the difference in operational pressure between the stripping step and the absorption step is suppressed to not more than 1,000 hPa (Effects and Advantages of the Invention)

The present invention can provide a process for producing a hydroxyalkyl (meth)acrylate which comprises the step of carrying out a reaction between (meth)acrylic acid and an alkylene oxide, wherein the process provides enablement for economically and efficiently recovering and recycling the unreacted residue of the alkylene oxide.

DETAILED DESCRIPTION OF THE PREFERRED EMBODIMENTS

Hereinafter; the present invention is more specifically illustrated by the following examples of some preferred embodiments in comparison with comparative examples not according to the invention. However, the present invention is not limited to the below-mentioned examples of some preferred embodiments.

EXAMPLE 1

An autoclave as equipped with stirring vanes was charged with 480 ml of an anion-exchange resin (DIAION PA316 produced by Mitsubishi Chemical Corporation) as a catalyst wherein the anion-exchange resin was in a water-swollen state. Then, 264 g/h of ethylene oxide and 288 g/h of acrylic acid (molar ratio of ethylene oxide/acrylic acid=1.5) were continuously supplied into the autoclave to carry out a reaction under conditions where the reaction temperature was 70° C. and where the residence time was 4.1 hours. The pressure during the reaction was about 4,200 hPa. The reacted liquid from the outlet of the autoclave was analyzed, with the result that the content of unreacted acrylic acid, the content of unreacted ethylene oxide, the conversion of acrylic acid, and the conversion of ethylene oxide were 2.6 weight %, 17.4 weight %, 95.0% and 63.7% respectively. As to by-products, the content of diester was 0.2 weight %, and the content of diethylene glycol monoacrylate was 1.5 weight %.

After being separated from the anion-exchange resin, the reacted liquid was supplied into a stripping column from its top wherein the stripping column had an operational pressure of 1,053 hPa, a column diameter of 32 mm, and a height of 40 cm, while 100 g/h of nitrogen gas having an oxygen concentration adjusted to 3 mol % was supplied from the column bottom to carry out the stripping step. The stripped column top gas was supplied into an absorption column from its bottom wherein the absorption column had an operational pressure of 1.013 hPa, a column diameter of 42 mm, and a height of 20 cm, while 850 g/h of pure water was supplied as an absorbing liquid from the column top. This pure water was supplied at 10° C. The liquid from the bottom of the stripping column was analyzed, with the result that the content of ethylene oxide was 0.02 weight %. This corresponds to an unreacted ethylene oxide stripping efficiency of 99.9%. The absorbing liquid from the bottom of the absorption column was analyzed, with the result that the content of ethylene oxide was 10.1 weight %. This corresponds to an unreacted ethylene oxide recovery efficiency of 99.7%. In addition, in the liquid resultant from the absorption, the acrylic acid concentration was 0.02 weight %, and the hydroxyethyl acrylate concentration was 0.05 weight %

This liquid resultant from the absorption was mixed with an aqueous solution having an ethylene oxide concentration of 10 weight % (flow rate=17 kg/h) and then supplied into an autoclave for an ethylene glycol formation reaction to carry out this reaction at a reaction temperature of 150° C. and a reaction pressure of about 30,000 hPa for a residence time of 0.4 hour. The reacted liquid from the outlet of the autoclave was analyzed, with the result that the ethylene oxide concentration was 0.01 weight %. This corresponds to a conversion of ethylene oxide of 99.9%. In addition, this reaction was carried out for 12 hours, but there occurred no deposition of polymers of acrylic acid and hydroxyethyl acrylate.

EXAMPLE 2

The sane operation as of Example 1 was carried out except that the rate of ethylene oxide as supplied into the autoclave was changed to 229 g/h (corresponding to molar ratio of ethylene oxide/acrylic acid 1.3) and that the residence time was changed to 4.8 hours. The reacted liquid from the outlet of the autoclave was analyzed, with the result that the content of unreacted acrylic acid, the content of unreacted ethylene oxide, the conversion of acrylic acid, and the conversion of ethylene oxide were 2.8 weight %, 11.7 weight %, 95.0% and 73.6% respectively. As to by-products, the content of diester was 0.22 weight %, and the content of diethylene glycol monoacrylate was 2.2 weight %.

The liquid from the bottom of the stripping column was analyzed, with the result that the content of ethylene oxide was 0.012 weight %. This corresponds to an unreacted ethylene oxide stripping efficiency of 99.9%. The absorbing liquid from the bottom of the absorption column was analyzed, with the result that the content of ethylene oxide was 6.6 weight %. This corresponds to an unreacted ethylene oxide recovery efficiency of 99.7%. In addition, in the liquid resultant from the absorption, the acrylic acid concentration was 0.02 weight %, and the hydroxyethyl acrylate concentration was 0.05 weight %.

This liquid resultant from the absorption was mixed with an aqueous solution having an ethylene oxide concentration of 10 weight % (flow rate=17 kg/h) and then supplied into an autoclave for an ethylene glycol formation reaction to carry out this reaction at a reaction temperature of 150° C. and a reaction pressure of about 30,000 hPa for a residence tine of 0.4 hour. The reacted liquid from the outlet of the autoclave was analyzed, with the result that the ethylene oxide concentration was 0.01 weight %. This corresponds to a conversion of ethylene oxide of 99.9%. In addition, this reaction was carried out for 12 hours, but there occurred no deposition of polymers of acrylic acid and hydroxyethyl acrylate,

EXAMPLE 3

The same operation as of Example 1 was carried out except that the residence time in the autoclave was changed to 3.2 hours and that the rate of the nitrogen gas as supplied into the stripping column was changed to 130 g/h. The reacted liquid from the outlet of the autoclave was analyzed, with the result that the content of unreacted acrylic acid, the content of unreacted ethylene oxide, the conversion of acrylic acid, and the conversion of ethylene oxide were 10.4 weight %, 22.2 weight %, 80.0% and 53.7% respectively. As to by-products, the content of diester was 0.13 weight %, and the content of diethylene glycol monoacrylate was 1.1 weight %.

The liquid from the bottom of the stripping column was analyzed, with the result that the content of ethylene oxide was 0.022 weight %. This corresponds to an unreacted ethylene oxide stripping efficiency of 99.9%. The absorbing liquid from the bottom of the absorption column was analyzed, with the result that the content of ethylene oxide was 12.4 weight %. This corresponds to an unreacted ethylene oxide recovery efficiency of 97.9%. In addition, in the liquid resultant from the absorption, the acrylic acid concentration was 0.22 weight %, and the hydroxyethyl acrylate concentration was 0.29 weight %.

This liquid resultant from the absorption was mixed with an aqueous solution having an ethylene oxide concentration of 10 weight % (flow rate=17 kg/h) and then supplied into an autoclave for an ethylene glycol formation reaction to carry out this reaction at a reaction temperature of 150° C. and a reaction pressure of about 30,000 hPa for a residence time of 0.4 hour. The reacted liquid from the outlet of the autoclave was analyzed, with the result that the ethylene oxide concentration was 0.01 weight %. This corresponds to a conversion of ethylene oxide of 99.9%. In addition, this reaction was carried out for 12 hours. As a result polymers flowed out of the outlet of the autoclave in a small amount of 1.1 g in total, but the apparatus could be worked stably without clogging up.

EXAMPLE 4

The same operation as of Example 1 was carried out except that the rate of the nitrogen gas as supplied into the stripping column was changed to 140 g/h.

The liquid from the bottom of the stripping column was analyzed, with the result that the content of ethylene oxide was 0.009 weight %. This corresponds to an unreacted ethylene oxide stripping efficiency of 99.95%. The absorbing liquid from the bottom of the absorption column was analyzed, with the result that the content of ethylene oxide was 10.0 weight %. This corresponds to an unreacted ethylene oxide recovery efficiency of 97.9%. In addition, in the liquid resultant from the absorption, the acrylic acid concentration was 0.15 weight %, and the hydroxyethyl acrylate concentration was 0.51 weight %.

This liquid resultant from the absorption was mixed with an aqueous solution having an ethylene oxide concentration of 10 weight % (flow rate=17 kg/h) and then supplied into an autoclave for an ethylene glycol formation reaction to carry out his reaction at a reaction temperature of 150° C. and a reaction pressure of about 30,000 hPa for a residence time of 0.4 hour. The reacted liquid from the outlet of the autoclave was analyzed, with the result that the ethylene oxide concentration was 0.01 weight % This corresponds to a conversion of ethylene oxide of 99.9%. In addition, this reaction was carried out for 12 hours. As a result, polymers flowed out of the outlet of the autoclave in a small amount of 1.8 g in total, but the apparatus could be worked stably without clogging up.

COMPARATIVE EXAMPLE 1

The, same operation as of Example 1 was carried out except that 288 g/h of acrylic acid was supplied as the absorbing liquid and that the ethylene glycol formation reaction was not carried out, wherein the flow rate of acrylic acid was determined on the assumption that acrylic acid would be recycled as a raw material for hydroxyethyl acrylate. The absorbing liquid from the bottom of the absorption column was analyzed, with the result that the content of ethylene oxide was 9.6 weight %. This corresponds to an unreacted ethylene oxide recovery efficiency of 32.0%.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing a hydroxyalkyl (meth)acrylate and an alkylene glycol, which comprises the steps of:
   a) carrying out a reaction between (meth)acrylic acid and an alkylene oxide to obtain a resultant reaction liquid comprising hydroxyalkyl (meth)acrylate;
   b) stripping alkylene oxide from the resultant reaction liquid to obtain stripped alkylene oxide as an unreacted residue;
   c) causing an absorbing solvent consisting essentially of water to absorb the stripped alkylene oxide under a pressure of 1000 to 2000 hPa to obtain an absorbing liquid resultant from absorption of the stripped alkylene oxide, wherein the absorbing liquid is an aqueous alkylene oxide solution;
   d) mixing the aqueous alkylene oxide solution with another aqueous alkylene oxide solution to obtain a mixture; and
   e) producing an alkylene glycol from the mixture.

2. A process according to claim 1, wherein the absorbing liquid resultant from the absorption of the unreacted residue of the alkylene oxide is mixed with an aqueous alkylene oxide solution resultant from production of an alkylene oxide and then used for the production of the alkylene glycol.

3. A process according to claim 1, wherein the (meth) acrylic acid concentration in the absorbing liquid resultant from absorption of the stripped alkylene oxide is not more than 0.2 weight %.

4. A process according to claim 1, wherein the hydroxyalkyl (meth)acrylate concentration in the absorbing liquid resultant from absorption of the stripped alkylene oxide is not more than 0.5 weight %.

5. A process for producing a hydroxyalkyl (meth)acrylate and an alkylene glycol, which comprises the steps of:
   a) carrying out a reaction between (meth)acrylic acid and an alkylene oxide to obtain a resultant reaction liquid comprising hydroxyalkyl (meth)acrylate;
   b) stripping alkylene oxide from the resultant reaction liquid to obtain stripped alkylene oxide as an unreacted residue;
   c) causing an absorbing solvent consisting essentially of water to absorb the stripped alkylene oxide to obtain an absorbing liquid resultant from absorption of the stripped alkylene oxide, wherein the absorbing liquid is an aqueous alkylene oxide solution; and
   d) producing an alkylene glycol using the absorbing liquid.

6. A process for producing a hydroxyalkyl (meth)acrylate and an alkylene glycol, which comprises the steps of:
   a) carrying out a reaction between (meth)acrylic acid and an alkylene oxide to obtain a resultant reaction liquid comprising hydroxyalkyl (meth)acrylate;
   b) stripping alkylene oxide from the resultant reaction liquid to obtain stripped alkylene oxide as an unreacted residue;
   c) causing an absorbing solvent consisting essentially of water to absorb the stripped alkylene oxide under a pressure of 1000 to 1950 hPa to obtain an absorbing liquid resultant from absorption of the stripped alkylene oxide, wherein the absorbing liquid is an aqueous alkylene oxide solution;
   d) mixing the aqueous alkylene oxide solution with another aqueous alkylene oxide solution to obtain a mixture; and
   e) producing an alkylene glycol from the mixture.

7. A process for producing a hydroxyalkyl (meth)acrylate, which comprises the steps of:
   a) carrying out a reaction between (meth)acrylic acid and an alkylene oxide to obtain a resultant reaction liquid comprising hydroxyalkyl (meth)acrylate;
   b) stripping alkylene oxide from the resultant reaction liquid to obtain stripped alkylene oxide as an unreacted residue;
   c) causing an absorbing solvent comprising water to absorb the stripped alkylene oxide to obtain an absorbing liquid resultant from absorption of the stripped alkylene oxide, wherein the absorbing liquid is an aqueous alkylene oxide solution and comprises water and the stripped alkylene oxide; and
   d) wherein the step of stripping is carried out at a first operational pressure, wherein the step of causing an absorbing solvent to absorb the stripped alkylene oxide is carried out at a second operational pressure, and wherein the second operational pressure is less than the first operational pressure.

* * * * *